United States Patent [19]

Cherukuri et al.

[11] Patent Number: 4,971,797
[45] Date of Patent: Nov. 20, 1990

[54] STABILIZED SUCRALOSE COMPLEX

[75] Inventors: Subraman R. Cherukuri, Towaco, N.J.; Lucy L. Wong, Jackson Heights, N.Y.

[73] Assignee: Warner-Lambert Company, Morris Plains, N.J.

[21] Appl. No.: 288,512

[22] Filed: Dec. 22, 1988

[51] Int. Cl.[5] ............................................. A61X 47/00
[52] U.S. Cl. ..................................... 424/440; 424/49; 424/439; 426/548; 426/590; 426/658
[58] Field of Search ................. 424/439, 48, 440, 49; 426/658, 548, 590; 536/18.5

[56] References Cited

U.S. PATENT DOCUMENTS

| | | | |
|---|---|---|---|
| 4,537,763 | 8/1985 | Miyake et al. | 424/64 |
| 4,725,387 | 2/1988 | Hirao et al. | 536/4.1 |
| 4,751,294 | 6/1988 | Jackson | 536/18.5 |
| 4,762,719 | 8/1988 | Forester | 424/451 |
| 4,786,491 | 11/1988 | Patel | 424/48 |
| 4,822,597 | 4/1989 | Faust et al. | 424/439 |

Primary Examiner—Thurman K. Page
Assistant Examiner—P. L. Prater
Attorney, Agent, or Firm—Daniel A. Scola, Jr.

[57] ABSTRACT

The chlorosucrose sweetener known as sucralose is prepared in a thermally stable composition by co-crystallization with a cyclodextrin. The resulting crystalline product may be comminuted to form particles of desired size for use as a sweetener component in place of or in addition to known sweeteners such as sucrose, saccharin and the like, in a variety of foods, comestibles, and oral medications. The preparation of the stabilized sucralose compositions of the present invention constitutes a molecular encapsulation of the sucralose within the cyclodextrin thereby protecting the sucralose from discoloration caused by heat. Numerous applications for this stabilized complex are suggested and disclosed.

25 Claims, 2 Drawing Sheets

SUCRALOSE/CYCLODEXTRIN CRYSTALLINE
MINS DELAYED DISCOLORATION VS. SUCRALOSE

STABILIZED SUCRALOSE COMPLEX

BACKGROUND OF THE INVENTION

The present invention relates to the preparation of chlorosucrose sweeteners and particularly to the preparation of such sweeteners in a stable form useful for incorporation in a variety of food and confectionery products as well as for medicinal uses.

The sweetening agent known as sucralose comprises a chlorosucrose sweetener derived from a class of compounds based upon sucrose and galactosucrose in which one or more hydroxy groups are replaced by chlorine atoms, and is described in U.K. Patent No. 1,543,167, the disclosure of which is incorporated herein by reference. Of particular interest is the compound sucralose, (4-chloro-4-deoxy-α-D-galactopyranosyl 1,6-dichloro1,6-dideoxy-β-D-fructofuranoside, also known as 4,1',6',-trichloro-4,1',6'-trideoxygalactosucrose). Sucralose and the other members of its chemical family have been identified as intensely sweet, offering a sweetness several hundred times that of sucrose, and are of particular interest for use as low calorie sweeteners to replace saccharin in various products, including foods, candy, comestibles, beverages and orally received medicinals such as cough drops.

This class of compounds is generally relatively stable and inert and particularly exhibits the stability in acid aqueous solutions, in marked contrast to peptide-based sweeteners such as aspartame. Under completely dry conditions, however, sucralose which is present in a crystalline form tends to discolor in response to elevated temperatures. For example, such discoloration can be exhibited after twenty minutes of exposure of pure dry sucralose to a temperature of 100C., wherein the color changes to a pale brown.

Efforts have previously been undertaken to stabilize sucralose by various techniques. For example, in U.K. Patent Application No. 2,169,601A to Jackson, sucralose is treated by co-crystallization with a nitrogenous base and in particular compounds containing an amine group such as niacinamide or an amino acid. An alternative approach was pursued by Jackson and Jenner and disclosed in European Patent Publication No. 0,255,260, wherein crystalline sucralose was prepared and then reduced to particles of critical dimension, in particular such particles no greater than 10 microns in mean particle size with a maximum particle size no greater than twice the mean.

Neither of the foregoing approaches has been totally satisfactory as the resulting sucralose products have continued to exhibit commercially undesirable thermal instability, and in the instance of the co-crystallization with the nitrogenous base material are further qualified in their acceptability by the admixture with a material that may be of reduced sweetness sensation.

A need therefore exists to develop a truly thermally stable form of sucralose that likewise maximizes the delivery of the sweetness sensation when such material is incorporated into foods and related comestible products.

SUMMARY OF THE INVENTION

In accordance with the present invention, a thermally stabilized composition is prepared which comprises a co-crystallized complex of sucralose and a cyclodextrin, preferably β(βCD). The co-crystallized complex comprises at least about 5% by weight of cyclodextrin and is prepared in particulate form to a uniform particle size. In a preferred embodiment, the co-crystallized complex comprises at least about 15% by weight of the cyclodextrin.

The complex may be prepared by dissolving a mixture of cyclodextrin and sucralose in a non-aqueous solvent such as methanol, followed by the removal of the methanol and the placement of the remaining slurry in a solvent such as ethyl acetate, filtering out the formed precipitate, washing the same with a further quantity of ethyl acetate and then drying the resulting crystals. Thereafter, the crystals may be ground down to the desired particle size and are ready for use.

The resulting crystalline complex exhibits extended thermal stability and can be incorporated into a variety of food, confectionery and medicinal products where sweeteners such as saccharin may be desirable. Accordingly, the present invention extends to such products having the complex included therein as an ingredient, such as anti-bacterial oral preparations and the like.

Accordingly, it is a principal object of the present invention to prepare a thermally stable form of the sweetener sucralose.

It is a still further object of the present invention to prepare the sweetener sucralose as aforesaid which exhibits extended thermal stability in conjunction with sweetness delivery comparable to that of the unmodified sweetener material.

It is a still further object of the present invention to provide a method for the preparation of a thermally stable complex of the sweetener sucralose which is simple and economical to perform.

It is a still further object of the present invention to prepare one or more comestible products containing a thermally stabilized complex including the sweetener sucralose.

It is a still further object of the present invention to prepare one or more food products containing a thermally stabilized complex of the sweetener sucralose.

It is a still further object of the present invention to prepare one or more medicinal products containing a thermally stabilized complex of the sweetener sucralose.

Other objects and advantages will become apparent to those skilled in the art from a review of the ensuring detailed description which proceeds with reference to the following illustrative drawings.

DETAILED DESCRIPTION

Figure 1:
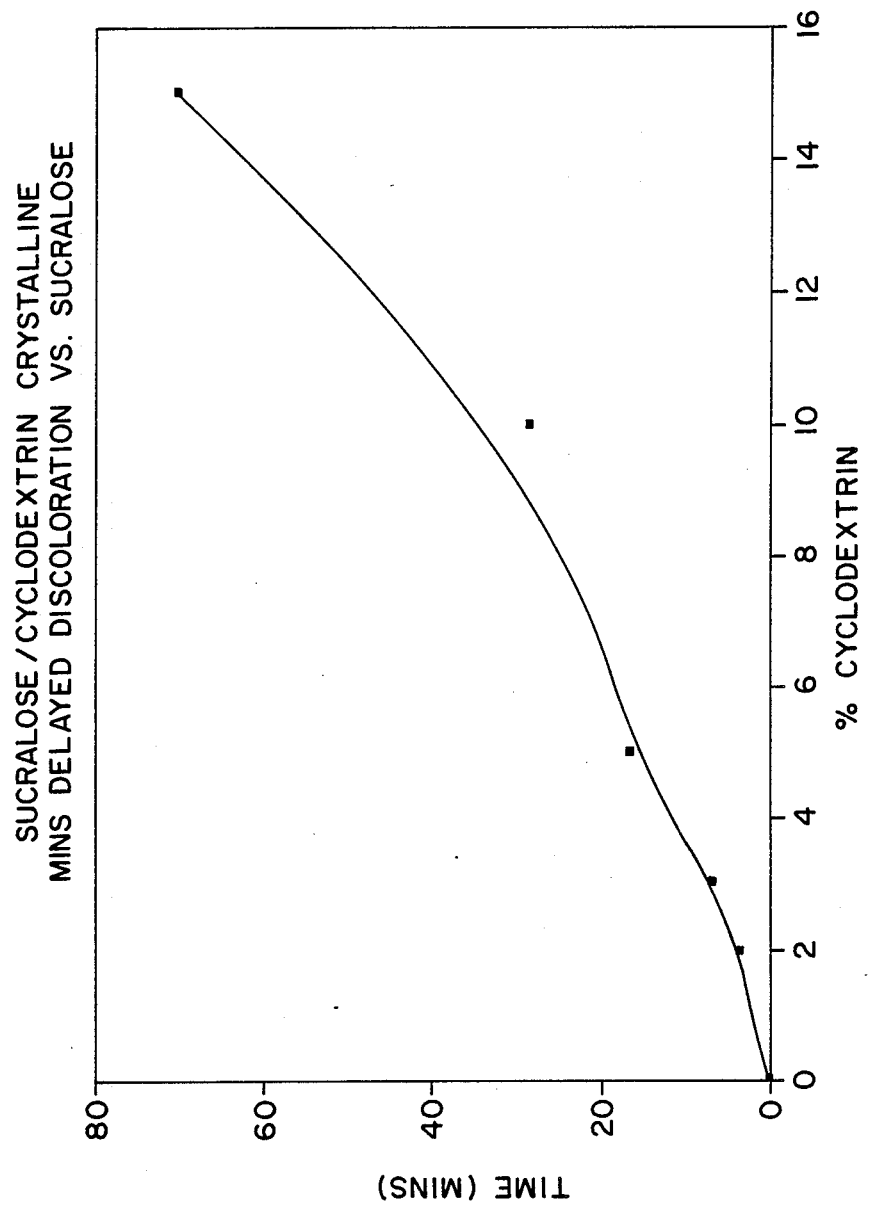
FIG. 1 is a graph depicting the improvement in resistance to browning of the co-crystalline complex of the present invention over pure sucralose.

As noted earlier, the present invention relates to preparation of the sweetener sucralose in a thermally stable form by the formation of a crystalline complex between sucralose and a cyclodextrin. More particularly, the complex constitutes a co-precipitate of the cyclodextrin and sucralose, with the cyclodextrin present in an amount of at least about 5% by weight, and more preferably at least about 15% by weight. The complex may be recovered and the resulting crystals may be comminuted to a uniform particle size. In a preferred embodiment, the particles have an average size on the order of about 10 microns.

The cyclodextrin used in the present invention (hereinafter abbreviated as CD) is a cyclic non-reducing oligosaccharide homolog formula of $(C_6H_{10}O_5)n$, joined by $\alpha$-1,4-glucosidic linkages to form a cyclic structure. Generally, 6 to 10 D-glucopyranose groups are bonded in this fashion, and form a rigid "doughnut-shaped" conical structure with a hollow interior of a specified volume. The resulting material is accordingly named $\alpha$-CD, $\beta$-CD or $\tau$-CD according to the degree of polymerization, i.e, 6, 7 or 8 glucose units. The interior of the ring contains C-H bonds or ether bonds and is thereby hydrophobic, while the exterior of the ring defines OH groups and is thereby hydrophilic. Because of its structure CD is able to entrap various compounds in its cyclic interior, and has recognized utility as a "molecular" encapsulant. For example, a variety of materials including aromatics, alcohols, halides and hydrogen halides, fatty acids and their esters are among the compounds that may be held within the internal cavity of cyclodextrin. The "guest" molecules must satisfy the size criterion of fitting at least partially into the cyclodextrin internal cavity, resulting in an inclusion complex.

CD has been used previously with foods to mask unwanted aromas, to prevent oxidation, to preserve flavors and to prevent moisture absorption, such as in sugared foods. CD has also found utility as a malodorous breath reducing agent, as as a stabilizer and bitterness reducer for citrus fruit and flavors.

The use of cyclodextrins in the functions indicated above is documented in the literature and, by way of example, attention is directed to Szejtli, J., "Cyclodextrins: A New Group of Industrial Basic Materials", DIE NAHRUNG, 29:9, 911–924 (1985); Nagamoto, S., "Cyclodextrins: Expanding the Development of Their Functions And Applications", CHEMICAL ECONOMY AND ENGINEERING REVIEW, Vol. 17, No. 7-8 (No. 190) pp. 28-35 (July/August 1985); U.S. Pat. No. 4,267,166, U.S. Pat. No. 4,332,825, U.S. Pat. No. 4,751,095, and lastly, European Patent Application, Publication No. 097,950 in the name of Ajinomoto Co., Inc. The first two articles deal generally with the structure and utility of cyclodextrins, and disclose the broad scope of its utility. U.S. Pat. No. 4,267,166 discloses the use of cyclodextrin as a foul breath preventive agent, while U.S. Pat. No. 4,332,825, Nagamoto Supra. and Konno, A., et al., "Bitterness Reduction of Citrus Fruits by $\beta$-Cyclodextrin", AGRIC. BIOL. CHEM., 45 (10): 2341-2342 (1981), disclose the ability of cyclodextrin to reduce the bitterness of citrus by forming inclusion complexes with bitter compounds such as naringin and limonin. Finally, U.S. Pat. No. 4,751,095 and the European Publication deal with the preparation of cyclodextrin complexes with aspartame. The last mentioned publications disclose the formation of stabilized inclusion complexes between the cyclodextrin and aspartame by the reaction of both materials in a common solvent, followed by drying of the formed complex, such drying being optional in the case of the European Publication. Both publications are distinguishable from the present invention in view of the obvious structural distinctions that exist between aspartame and sucralose and more particularly, the manner in which the complexes of the present invention are prepared.

CD is usually produced from starch by treating it with an amylase or similar enzyme produced from *Bacillus macerans* or an alkali-resistant bacterium. Although there are no particular limitations on the CD that can be used in the present invention, one can choose the particular CD, i.e. $\alpha$-CD, $\beta$-CD or $\tau$-CD depending upon the solubility of the resulting complex that one wishes to achieve. The respective cyclodextrins may be employed as a mixture in some instances, or when the use of a particular cyclodextrin is not critical. In the instance where the present complex is to be used as a food additive, $\beta$CD is preferred.

As noted earlier, the co-crystallized complex of sucralose and cyclodextrin may be prepared simply by the formation of a solution of both ingredients in a non-aqueous solvent such as methanol, the removal of the solvent and the placement of the resulting slurry in a solution with ethyl acetate, all of which may be conducted at room temperature. The ingredients may be added and retained therein for a period of time sufficient to permit co-crystallization to take place. Naturally, the temperature of the solution should not be unduly raised as discoloration of the sucralose component could occur.

More particularly, the inventive method comprises:

(a) dissolving a quantity of sucralose and a stoichiometrically sufficient amount of a cyclodextrin in a suitable non-aqueous solvent;

(b) maintaining the solution formed in step (a) for a period of time sufficient to permit full co-crystallization of said sucralose and said cyclodextrin to take place;

(c) recovering the crystalline reaction product from step (b) and drying the same; and (d) subjecting the material from step (d) to comminution to form particles therefrom.

The ethyl acetate solution may be optionally subjected to stirring and may likewise be reduced in temperature and maintained under such conditions for a period of hours to allow crystallization to take place. Upon completion of crystal formation, the reaction product may be recovered such as by filtration, optionally washed with a further quantity of ethyl acetate and then dried. After drying is complete, the resulting crystals may be comminuted to uniform particle sizes, and thereafter transferred for storage or incorporation into various products.

The complexes prepared in accordance with the present invention are suitable for use in any aqueous food to replace sugars normally used as sweeteners. The term "aqueous foods" as used herein refers to all foods except dried foods and oily foods, and by way of non-limiting example, includes beverages such as fruit juices, such as citrus juices, vegetable juices such as tomato juice, cola, sports drinks (i.e. isotonically balanced drinks), coffee, tea, cocoa, dairy milk and milk-containing drinks, ginger ale; yogurt, jelly, puddings and mousse; sauces such as ketchup, mayonnaise, salad dressings, fruit-flavored sauce, chocolate sauce, tomato sauce and chili sauce; creams, toppings, fillings and jams; frozen desserts such as ice creams and sherbets; pickle syrups, and pickling syrup; chewing gum, hard candies, nougat candies, jelly beans and the like.

In the instance where the complex of the present invention is to be incorporated in a chewing gum, the gum base may be any chewable, substantially water-insoluble base such as chicle or substitutes thereof, gut-tagkay, sorva, jelutong, synthetic resins, rubbers and the like and mixtures of these materials. The amount of gum base employed in the chewing gum may vary depending upon the particular base utilized and the other ingredients that make up the final product. Generally, however, the gum base may vary in amount from about 15 to 40% by weight of the final composition, and preferably from about 20 to about 30% by weight.

Plasticizers or softeners such as lanolin, propylene, glycol, glycerol and the like and mixtures of these may optionally be incorporated within the gum base to achieve desired texture and consistency. The flavors employed in chewing gums may be the essential oils or synthetic flavors or mixtures of these. Flavors such as cinnamon, wintergreen, spearmint, peppermint, birch, anise, fruit flavors and the like may be utilized satisfactorily. The amount of flavoring is a matter of preference, but may be subject to such factors as the type of flavor and the type of base utilized in conjunction therewith. Generally, flavoring materials account for about 1% by weight of the total gum composition.

As it is generally desirable that the chewing gum possess a distinct and favorable sweetness, the remaining portion of the chewing gum is generally composed of water soluble carbohydrates, particularly bulk sweeteners such as sugar or sugar alcohols. Thus, in addition to the incorporation of the inventive co-crystallized complex of sucralose and CD, various sweeteners well-known in the art for their bulking and/or sweetening ability. For example, sugared chewing gum compositions may include sucrose, dextrose, corn syrup, galactose, glucose, fructose and substitutes, and mixtures thereof. Sugar substitutes may include any sweetening agents utilized in sugarless gum such as mannitol, sorbitol, xylitol, acid saccharin and its salts, cyclamates, and dipeptides such as aspartame, dihydrochalcone, glycyrrhizin, and *Stevia rebaudiana* (Stevioside). Also contemplated as an additional sweetener is the non-fermentable sugar substitute (hydrogenated starch hydrolysate) which is described in U.S. Reissue Pat. No. 26,959, and the synthetic sweetener 3,4-dihydro-6-methyl-1,2,3-oxathiazin-4-one-2,2-dioxide (acesulfame-K) particularly the potassium, sodium and calcium salts thereof as described in German Patent No. 2,001,017.7.

In the instance where the sucralose complex of the present invention is to be incorporated in a chewing gum, it may be utilized in an amount ranging from about 0.02 to about 0.25%, and will offer satisfactory sweetness. Naturally, the exact amount of sucralose complex incorporated in a given chewing gum may vary depending upon the desired sweetness level.

In addition, the complexes of the present invention can be incorporated into aqueous or aqueous-alcohol oral preparations such as mouthwashes, sprays, rinses, tooth pastes, dental creams or tooth powders. In such event, the complex should be present in amounts ranging from 0.01% to about 40% by weight and more preferably, from about 5% to about 40% by weight of the final composition.

Oral preparations to which the inventive complex may be added can take a variety of textural forms. For example, in the case of dental creams, tooth pastes or tooth powders, the texture may be grainy or pasty. Likewise, gel-like preparations may be formulated utilizing agents such as colloidal silica and alkali metal alumino silicates.

As indicated with respect to chewing gums, the stabilized sucralose complex of the present invention is preferably used in conjunction with known natural and artificial sweeteners such as sucrose, saccharides, saccharin, acesulfame-K, aspartame and the like.

The present invention will now be better understood by reference to certain specific examples which are presented hereinafter for purposes of illustration and not limitation. In the examples, all percentages and parts as given, are expressed by weight unless otherwise stated.

EXAMPLE I

Several stabilized sucralose compositions were prepared by the following procedure. A quantity of $\beta$ was added to sucralose and the resulting mixture was then dissolved in 25 ml. methanol and thereafter heated to 40.C. with the application of vacuum suction to draw off the methanol. After 1 hour the remaining slurry was dissolved in ethyl acetate and the resulting solution was heated to complete the formation of the solution. The solution was then cooled to 20.C. and allowed to crystallize overnight in a refrigerator. The crystalline precipitate was then filtered off by cold-filtration, and thereafter air-dried and then milled to a uniform particle size.

A series of samples of co-crystalline complexes were prepared for testing, and accordingly 0.25, 0.5 and 1.0 g of cyclodextrin were added to sucralose to prepare a total of 5 g of mixture. The samples thus corresponded to mixtures containing 5%, 10% and 20% cyclodextrin. As a comparison, a sample containing pure sucralose was prepared in the same manner, and was likewise milled identically to eliminate any particle size differences.

The powders thus prepared were subjected to a temperature of about 195 F (92.C.) and were monitored during heating to note the length of time that it took for the respective samples to turn light brown and to thereby discolor. The results are set forth in Table 1, below.

TABLE 1

| SAMPLE | ELAPSED TIME BEFORE DISCOLORATION |
| --- | --- |
| SUCRALOSE ALONE | 60 Minutes |
| SUCRALOSE-5% CYCLODEXTRIN | 80 Minutes |
| SUCRALOSE-10% CYCLODEXTRIN | 90 Minutes |
| SUCRALOSE-20% CYCLODEXTRIN | 180 Minutes |

Referring to Table 1, it is apparent that a 33.3% improvement in thermal stability as reflected in resistance to discoloration is achieved by the co-crystallization of sucralose with as little as 5% cyclodextrin, with a 50% improvement results from the use of 10% cyclodextrin. The most dramatic improvement of 300% was seen when co-crystallization was conducted with 20% by weight of cyclodextrin. A complex containing only 1% cyclodextrin was also prepared and tested, and although the data was not presented above, it indicated that such a minimal concentration of cyclodextrin was largely ineffective.

Lastly, it was noted that the measurements and results presented herein were more apparent when the tests were conducted at the lower temperature range selected.

EXAMPLE II

Additional thermal stability testing was conducted between a free sucralose control and inventive samples containing 2%, 3%, 5%, 10% and 15% cyclodextrin, respectively, for the purpose of confirming the results of the tests conducted in Example 1, and to determine the activity and effectiveness of inventive complexes prepared with other variant cyclodextrin contents. The preparation of the control and inventive samples was the same as that employed with the samples of Example 1. The temperature applied during the stability test was 195° F.±5.F. The results are set forth in Table 2 below, as well as in FIG. 1, which represents a plot of time delay in discoloration of the inventive samples over the control sample of pure sucralose.

TABLE 2

| SAMPLE | ELAPSED TIME BEFORE DISCOLORATION | MINUTES DELAYED VS. FREE SUCRALOSE |
| --- | --- | --- |
| SUCRALOSE ALONE | 65 Minutes | 0 |
| SUCRALOSE-2% CYCLODEXTRIN | 69 Minutes | 4 |
| SUCRALOSE-3% CYCLODEXTRIN | 72 Minutes | 7 |
| SUCRALOSE-5% CYCLODEXTRIN | 82 Minutes | 17 |
| SUCRALOSE-10% CYCLODEXTRIN | 94 Minutes | 29 |
| SUCRALOSE-15% CYCLODEXTRIN | 136 Minutes | 71 |

The data presented above and in FIG. 1 further confirm the threshold of significant thermal stability exhibited by the use of 5% cyclodextrin, and also demonstrates a substantial improvement in stability as the level of cyclodextrin is increased from 10% to 15%.

EXAMPLE III

In this Example, a comparison was made between complexes of the present invention that differed as to the quantity of cyclodextrin present, to determine whether the presence of cyclodextrin has any effect on the sweetness intensity and delivery of the sucralose component. Accordingly, 0.29 g of a complex containing 5% cyclodextrin and 0.31 g of a complex containing 10% cyclodextrin were separately dissolved in 100 g of water to form equivalent solutions of 0.28% sucralose content. A solution containing 0.28% of free sucralose was also prepared and tested.

Equal samples of each of the solutions were given to an expert panel. The panel concluded that all of the solutions were sweet and noted no differences among the respective solutions. From the above results, it can be concluded that cyclodextrin in these amounts does not diminish the sweetness delivery and sensation offered by sucralose.

EXAMPLE IV

The sweetness intensity of the invention in a gum formulation was compared herein with that of free sucralose, a co-crystalline complex of sucralose and niacinamide, the latter prepared in accordance with the procedures taught in the United Kingdom Application No. 2,169,601A to Jackson, disclosed earlier herein. Specifically, samples of the inventive complex containing 5% cyclodextrin, free sucralose and the complex of Jackson publication prepared with 3% by weight of niacinamide, were respectively formulated and incorporated into otherwise identical spearmint flavored chewing gums in equal amounts and by equally identical procedures. After formulation, the gum samples were subjected to expert chew panel evaluation of sweetness intensity.

Accordingly, the gum samples were given to a panel of scientists, all of whom chew on a regular basis for the purpose of screening the samples. During the experiment each panelist was asked to evaluate the sweetness intensity of each of the samples and to render an opinion based on the following numerical values.

| 0 | 10 | 20 | 30 | 40 | 50 | 60 | 70 | 80 | 90 | 100 |
| --- | --- | --- | --- | --- | --- | --- | --- | --- | --- | --- |
| LOWEST SWEETNESS | | | | | | | | | | HIGHEST SWEETNESS |

The panelists were asked to rate the samples at intervals of 30 seconds, 2 minutes and 6 minutes. The results of the ratings assigned by each of the panelists to each of the samples were averaged together and then compared. The data are expressed in graphical form in FIG. 2.

Figure 2:
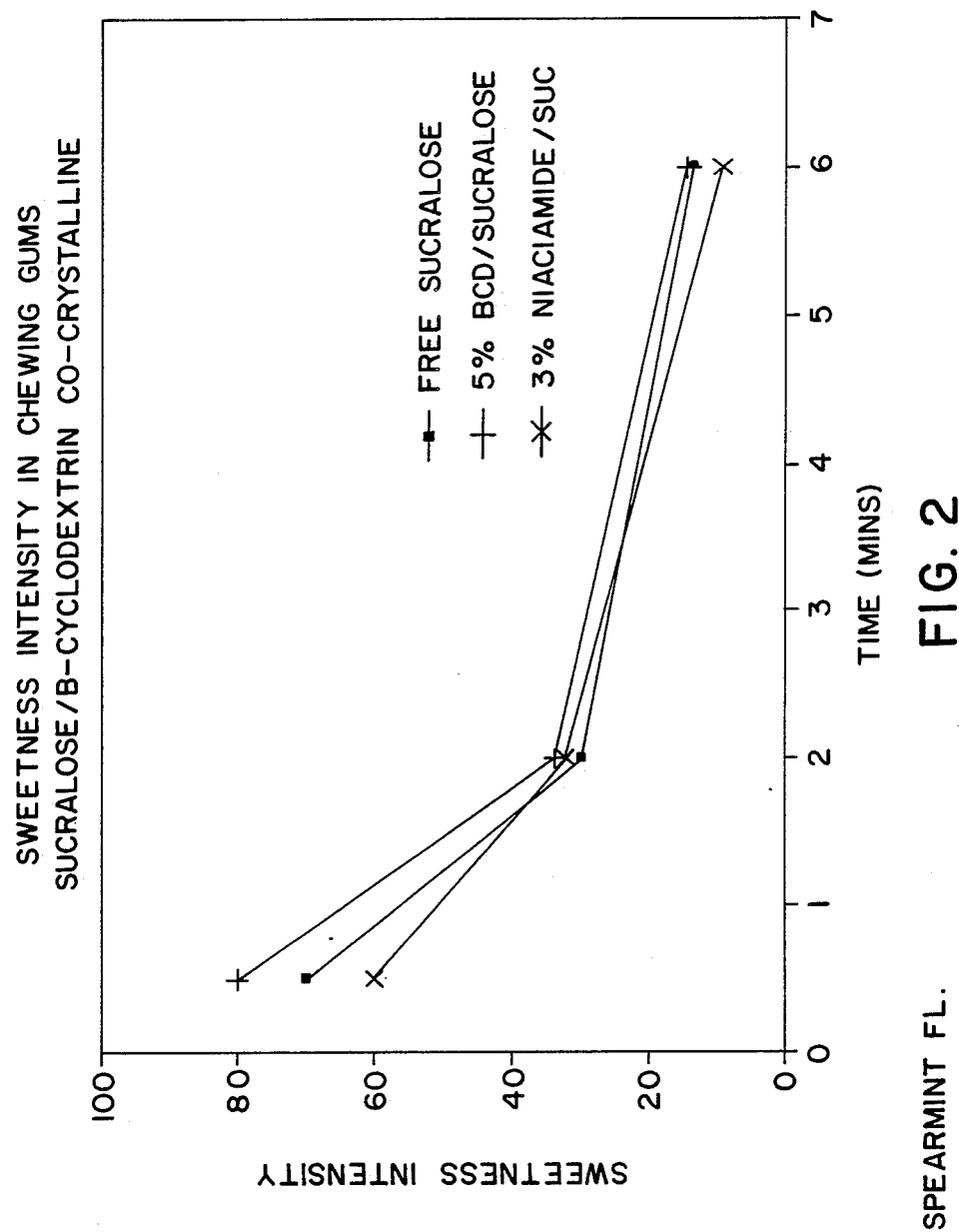
FIG. 2 is a graph presenting the results of comparative testing of the sweetness intensity of chewing gums embodying the complex of the present invention with gums employing commercially available forms of sucralose.

As can be seen from FIG. 2, the sample containing the inventive sucralose complex was rated better as to sweetness than both of the other samples. Accordingly, the present complex offered an initial sweetness that was greater than free sucralose. By comparison, the sample prepared in accordance with the Jackson disclosure offered the lowest initial sweetness intensity.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A thermally stabilized sucralose composition comprising a co-crystallized complex of sucralose and at least about 5% by weight of a cyclodextrin.

2. The composition of claim 1 wherein said cyclodextrin is selected from the group consisting of α-cyclodextrin, β-cyclodextrin, τ-cyclodextrin and mixtures thereof.

3. The composition of claim 1 wherein part or all of said sucralose is entrapped within said cyclodextrin.

4. The composition of claim 1 wherein said complex contains at least about 15% by weight of said cyclodextrin.

5. The composition of claim 1 prepared in particulate form.

6. The composition of claim 5 wherein said complex possesses a particle size on the order of about 10 microns.

7. A method for the preparation of a thermally stabilized sucralose composition, comprising:
 (a) dissolving a quantity of sucralose and a stoichiometrically sufficient amount of a cyclodextrin in a suitable non-aqueous solvent;
 (b) maintaining the solution formed in step (a) for a period of time sufficient to permit full co-crystallization of said sucralose and said cyclodextrin to take place;

(c) recovering the crystalline reaction product from step (b) and drying the same; and (d) subjecting the material from step (d) to comminution to form particles therefrom.

8. The method of claim 7 wherein said cyclodextrin is selected from the group consisting of α-cyclodextrin, β-cyclodextrin, τ-cyclodextrin and mixtures thereof.

9. The method of claim 7 wherein the resulting particles contain at least about 5% by weight of cyclodextrin.

10. The method of claim 7 wherein the resulting particles contain at least about 15% by weight of cyclodextrin.

11. The method of claim 7 wherein said non-aqueous solvent is selected from the group consisting of methanol and ethyl acetate.

12. The method of claim 7 wherein said non-aqueous solvent comprises methanol and ethyl acetate.

13. The method of claim 7 wherein said solution is maintained for up to about eight hours.

14. The method of claim 7 wherein said solution contains ethyl acetate and is maintained at a reduced temperature for a period on the order of about eight hours.

15. The method of claim 7 wherein the particles have an average size of about 10 microns.

16. A solid food containing a sweetener, the sweetener comprising the thermally stabilized composition of claim 1.

17. An aqueous food containing a sweetener, the sweetener comprising the thermally stabilized composition of claim 1.

18. A liquid beverage containing a sweetener, the sweetener comprising the thermally stabilized composition of claim 1.

19. A chewing gum composition containing a sweetener, the sweetener comprising the thermally stabilized composition of claim 1.

20. A mouth wash containing a sweetener, the sweetener comprising the thermally stabilized composition of claim 1.

21. A cough drop containing a sweetener, the sweetener comprising the stabilized composition of claim 1.

22. A confectionary preparation containing a sweetener, the sweetener comprising the thermally stabilized composition of claim 1.

23. The confectionary preparation of claim 22 selected from the group consisting hard candy, soft candy, chocolate and cookies.

24. A breath mint containing a sweetener, the sweetener comprising the thermally stabilized composition of claim 1.

25. An orally ingestible pharmaceutical preparation containing a sweetener, the sweetener comprising the stabilized composition of claim 1.

* * * * *